united States Patent [19]

Lorenzetti et al.

[11] Patent Number: 5,529,932

[45] Date of Patent: Jun. 25, 1996

[54] ISOLATED DNA ENCODING A PLANT RIBOSOME INACTIVATING PROTEIN FROM THE LEAVES OF SAPONARIA OFFICINALIS

[75] Inventors: Rolando Lorenzetti, Monza Mi; Luca Benatti, San Maurizio Al Lambro; Maria Dian; Douglas Lappi, both of Milan; Maria B. Saccardo, Saronno, Va; Marco Soria, Milan, all of Italy

[73] Assignee: Pharmacia, S.p.A., Milan, Italy

[21] Appl. No.: 133,278

[22] Filed: Oct. 7, 1993

Related U.S. Application Data

[63] Continuation of Ser. No. 885,242, May 20, 1992, abandoned, which is a continuation of Ser. No. 302,901, Jan. 30, 1989, abandoned.

[30] Foreign Application Priority Data

Jan. 28, 1988 [GB] United Kingdom ............. 8801877

[51] Int. Cl.⁶ ..................... C12N 15/29; C12N 15/70
[52] U.S. Cl. .............. 435/320.1; 435/69.1; 435/172.3; 435/252.33; 536/23.6
[58] Field of Search ................. 435/252.33, 172.3, 435/320.1, 69.1, 69.7; 536/23.1, 23.4, 23.6

[56] References Cited

U.S. PATENT DOCUMENTS

| | | | |
|---|---|---|---|
| 4,468,382 | 8/1984 | Bacha et al. | 514/19 |
| 4,962,188 | 10/1990 | Frankel | 530/389 |
| 5,087,616 | 2/1992 | Myers et al. | 514/21 |
| 5,191,067 | 3/1993 | Lappi et al. | 530/399 |
| 5,308,622 | 5/1994 | Cassells et al. | 424/422 |

FOREIGN PATENT DOCUMENTS

| | | |
|---|---|---|
| 2194241 | 3/1988 | United Kingdom . |
| 2216891 | 10/1989 | United Kingdom . |
| 9325688 | 12/1993 | WIPO . |

OTHER PUBLICATIONS

Benatti et al. Eur. J. Biochem. 183:465–470 (1989).

(List continued on next page.)

Primary Examiner—John L. LeGuyader
Attorney, Agent, or Firm—Seed and Berry

[57] ABSTRACT

Nucleic acid encoding the ribosome-inactivating protein SO-6 is provided. In particular, DNA that has the following sequence of nucleotides is provided:

```
1                           24
GTCACATCAA TCACATTAGA TCTAGTAAAT
                50
CCGACCGCGG GTCAATACTC ATCTTTTGTG
GATAAAATCC GAAACAACGT AAAGGATCCA
```

-continued
```
              100
AACCTGAAAT ACGGTGGTAC CGACATAGCC
                              150
GTGATAGGCC CACCTTCTAA AGAAAAATTC
CTTAGAATTA ATTTCCAAAG TTCCCGAGGA
              200
ACGGTCTCAC TTGGCCTAAA ACGCGATAAC
TTGTATGTGG TCGCGTATCT TGCAATGGAT
         250
AACACGAATG TTAATCGGGC ATATTACTTC
                              300
AGATCAGAAA TTACTTCCGC CGAGTCAACC
GCCCTTTTCC CAGAGGCCAC AACTGCAAAT
              350
CAGAAAGCTT TAGAATACAC AGAAGATTAT
CAGTCGATTG AAAAGAATGC CCAGATAACA
    400
CAAGGAGATC AAAGTAGAAA AGAACTCGGG
                              450
TTGGGGATTG ACTTACTTTC AACGTCCATG
GAAGCAGTGA ACAAGAAGGC ACGTGTGGTT
              500
AAAGACGAAG CTAGATTCCT TCTTATCGCT
ATTCAGATGA CGGCTGAGGC AGCGCGATTT
         550
AGGTACATAC AAAACTTGGT AATCAAGAAC
                              600
TTTCCCAACA AGTTCAACTC GGAAAACAAA
GTGATTCAGT TTGAGGTTAA CTGGAAAAAA
              650
ATTTCTACGG CAATATACGG GGATGCCAAA
AACGGCGTGT TTAATAAAGA TTATGATTTC
    700
GGGTTTGGAA AAGTTAGGCA GGTGAAGGAC
                              750
TTGCAAATGG GACTCCTTAT GTATTTGGGC
              768
AAACCAAAGT CGTCAAAC.
```

5 Claims, 5 Drawing Sheets

OTHER PUBLICATIONS

Maniatis et al. Molecular Cloning: a laboratory mannal, Cold Spring Harbor Laboratory, CSH, New York, 1982, pp. 412–413 & 422.Barbieri and Strip, "Ribosome–inactivating proteins from plants: Properties and possible uses," *Cancer Surveys* 1(3):490–520 (1982).

Lambert et al., "Immunotoxins containing single chain ribosome–inactivating proteins", *Cancer Treatment* 37:175–209 (1988) (Review Article, pub. subsequent to effective filing date of appln.)

Lambert et al., "Purified immunotoxins that are reactive with human lymphoid cells," *J. Biol. Chem.* 260(22):12035–12041 (1985).

Lappi et al., "The disulfide bond connecting the chains of ricin," *Proc. Natl. Acad. Sci. USA* 75(3):1096–1100 (1978).

Stripe et al., "hepatotoxicity of immunotoxins made with saporin, a ribosome inactivating protein from *Saponaria Officinalis, Virchows* i Archiv B "53:259–271 (1987).

Thorpe et al., "Cytotoxicity acquired by conjugation of an anti–$Thy_{1,1}$ monoclonal antibody and the ribosome–inactivating protein, gelonin," *Eur. J. Biochem.* 116:447–454 (1981).

Homandberg et al. Biochemistry 21:3385–3389 (1982).

Webster's Ninth New Collegiate Dictionary, Merriam–Webster Inc., (1990).

Abs. 15th Annual UCLA Symposium on Molecular and Cellular Biology, Park Utah, Lappi et al.

Chang et al., Proc. Natl. Acad. Sci, USA vol 84 pp. 5640–5644.(1987).

Old et al., Principles of Gene Manipulation, Blackwell Sci. Publ., Oxford, Engand, 3rd ed., (1985).

Lappi et al., Biochem, Biophys. Res. Comm. vol. 129, No. 3, pp. 934–94 (1985).

Chemical Abstracts, vol. 103, #51233f (1985).

CNBr1

Val Thr Ser Ile Thr Leu Asp Leu Val Asn Pro Thr Ala Gly Gln Tyr
Ser Ser Phe Val Asp Lys Ile Arg Asn Asn Val Lys Asp Pro Asn Leu
Lys Tyr Gly Gly Thr Asp Ile Ala Val Ile Gly Pro

CNBr2

Glu Ala Val Asn Lys Lys Ala Arg Val Val Lys Asn Glu Ala Arg Phe

CNBr3

Ser Asp Glu Asn Ala Arg Phe Arg Tyr Ile Gln Asn Leu Val Arg Lys

CNBr4

Arg Lys Ile Ser Thr Ala Ile Tyr Gly Asp Ala Lys Asn Gly Val Phe
Asn Lys Asp Tyr Asp Phe Gly Phe Gly Lys Val Arg Gln Val Lys Asp
Leu Gln

CNBr5

Tyr Leu Gly Lys Pro Lys Ser Ser Asn

```
ATCGTACAAC GTTCATCACT AGAA ATG AAG ATA TAT GTT GTA GCC ACA ATA         -46
                          Met Lys Ile Tyr Val Val Ala Thr Ile
                                         -20

GCA TGG ATC CTG CTT CAA TTT TCA GCT TGG ACA ACA ACT GAT GCG GTC          3
Ala Trp Ile Leu Leu Gln Phe Ser Ala Trp Thr Thr Thr Asp Ala Val
-15              -10                 -5                        1

ACA TCA ATC ACA TTA GAT CTA GTA AAT CCG ACC GCG GGT CAA TAC TCA         51
Thr Ser Ile Thr Leu Asp Leu Val Asn Pro Thr Ala Gly Gln Tyr Ser
             5                  10                  15

TCT TTT GTG GAT AAA ATC CGA AAC AAC GTA AAG GAT CCA AAC CTG AAA         99
Ser Phe Val Asp Lys Ile Arg Asn Asn Val Lys Asp Pro Asn Leu Lys
         20                  25                  30

TAC GGT GGT ACC GAC ATA GCC GTG ATA GGC CCA CCT TCT AAA GAA AAA        147
Tyr Gly Gly Thr Asp Ile Ala Val Ile Gly Pro Pro Ser Lys Glu Lys
         35                  40                  45

TTC CTT AGA ATT AAT TTC CAA AGT TCC CGA GGA ACG GTC TCA CTT GGC        195
Phe Leu Arg Ile Asn Phe Gln Ser Ser Arg Gly Thr Val Ser Leu Gly
 50                  55                  60                  65

CTA AAA CGC GAT AAC TTG TAT GTG GTC GCG TAT CTT GCA ATG GAT AAC        243
Leu Lys Arg Asp Asn Leu Tyr Val Val Ala Tyr Leu Ala Met Asp Asn
                 70                  80                  85

ACG AAT GTT AAT CGG GCA TAT TAC TTC AGA TCA GAA ATT ACT TCC GCC        291
Thr Asn Val Asn Arg Ala Tyr Tyr Phe Arg Ser Glu Ile Thr Ser Ala
             90                  95                 100

GAG TCA ACC GCC CTT TTC CCA GAG GCC ACA ACT GCA AAT CAG AAA GCT        339
Glu Ser Thr Ala Leu Phe Pro Glu Ala Thr Thr Ala Asn Gln Lys Ala
        105                 110                 115

TTA GAA TAC ACA GAA GAT TAT CAG TCG ATT GAA AAG AAT GCC CAG ATA        387
Leu Glu Tyr Thr Glu Asp Tyr Gln Ser Ile Glu Lys Asn Ala Gln Ile
        120                 125                 130

ACA CAA GGA GAT CAA AGT AGA AAA GAA CTC GGG TTG GGG ATT GAC TTA        435
Thr Gln Gly Asp Gln Ser Arg Lys Glu Leu Gly Leu Gly Ile Asp Leu
135                 140                 145                 150

CTT TCA ACG TCC ATG GAA GCA GTG AAC AAG AAG GCA CGT GTG GTT AAA        481
Leu Ser Thr Ser Met Glu Ala Val Asn Lys Lys Ala Arg Val Val Lys
                155                 160                 165
```

*Fig. 3a*

| | |
|---|---|
| GAC GAA GCT AGA TTC CTT CTT ATC GCT ATT CAG ATG ACG GCT GAG GCA<br>Asp Glu Ala Arg Phe Leu Leu Ile Ala Ile Gln Met Thr Ala Glu Ala<br>             170                     175                180 | 529 |
| GCG CGA TTT AGG TAC ATA CAA AAC TTG GTA ATC AAG AAC TTT CCC AAC<br>Ala Arg Phe Arg Tyr Ile Gln Asn Leu Val Ile Lys Asn Phe Pro Asn<br>             185                     190                195 | 577 |
| AAG TTC AAC TCG GAA AAC AAA GTG ATT CAG TTT GAG GTT AAC TGG AAA<br>Lys Phe Asn Ser Glu Asn Lys Val Ile Gln Phe Glu Val Asn Trp Lys<br>    200                     205                   210 | 625 |
| AAA ATT TCT ACG GCA ATA TAC GGG GAT GCC AAA AAC GGC GTG TTT AAT<br>Lys Ile Ser Thr Ala Ile Tyr Gly Asp Ala Lys Asn Gly Val Phe Asn<br>215                   220                   225                230 | 673 |
| AAA GAT TAT GAT TTC GGG TTT GGA AAA GTT AGG CAG GTG AAG GAC TTG<br>Lys Asp Tyr Asp Phe Gly Phe Gly Lys Val Arg Gln Val Lys Asp Leu<br>             235                     240                245 | 721 |
| CAA ATG GGA CTC CTT ATG TAT TTG GGC AAA CCA AAG TCG TCA AAC<br>Gln Met Gly Leu Leu Met Tyr Leu Gly Lys Pro Lys Ser Ser Asn<br>             250                     255                260 | 766 |

*Fig. 3b*

```
                                                                              20
Val Thr Ser Ile Thr Leu Asp Leu Val Asn Pro Thr Ala Gly Gln Tyr Ser Ser Phe Val
Val Thr Ser Ile Thr Leu Asp Leu Val Asn Pro Thr Ala Gly Gln Tyr Ser Ser Phe Val
                                                                              40
Asp Lys Ile Arg Asn Asn Val Lys Asp Pro Asn Leu Lys Tyr Gly Gly Thr Asp Ile Ala
Asp Lys Ile Arg Asn Asn Val Lys Asp Pro Asn Leu Lys Tyr Gly Gly Thr Asp Ile Ala
                                                                              60
Val Ile Gly Pro Pro Ser Lys Glu Lys Phe Leu Arg Ile Asn Phe Gln Ser Ser Arg Gly
Val Ile Gly Pro
                                                                              80
Thr Val Ser Leu Gly Leu Lys Arg Asp Asn Leu Tyr Val Val Ala Tyr Leu Ala Met Asp

100
Asn Thr Asn Val Asn Arg Ala Tyr Tyr Phe Arg Ser Glu Ile Thr Ser Ala Glu Ser Thr

120
Ala Leu Phe Pro Glu Ala Thr Thr Ala Asn Gln Lys Ala Leu Glu Tyr Thr Glu Asp Tyr

140
Gln Ser Ile Glu Lys Asn Ala Gln Ile Thr Gln Gly Asp Gln Ser Arg Lys Glu Leu Gly

160
Leu Gly Ile Asp Leu Leu Ser Thr Ser Met Glu Ala Val Asn Lys Lys Ala Arg Val Val
                                        Glu Ala Val Asn Lys Lys Ala Arg Val Val
                                                                             180
Lys Asp Glu Ala Arg Phe Leu Leu Ile Ala Ile Gln Met Thr Ala Glu Ala Ala Arg Phe
Lys Asn Glu Ala Arg Phe                                Ser Asp Glu Asn Ala Arg Phe
    *                                                   * *
                                                                             200
Arg Tyr Ile Gln Asn Leu Val Ile Lys Asn Phe Pro Asn Lys Phe Asn Ser Glu Asn Lys
Arg Tyr Ile Gln Asn Leu Val Arg Lys
                              *
                                                                             220
Val Ile Gln Phe Glu Val Asn Trp Lys Lys Ile Ser Thr Ala Ile Tyr Gly Asp Ala Lys
                            Arg Lys Ile Ser Thr Ala Ile Tyr Gly Asp Ala Lys
                              *
                                                                             240
Asn Gly Val Phe Asn Lys Asp Tyr Asp Phe Gly Phe Gly Lys Val Arg Gln Val Lys Asp
Asn Gly Val Phe Asn Lys Asp Tyr Asp Phe Gly Phe Gly Lys Val Arg Gln Val Lys Asp

Leu Gln Met Gly Leu Leu Met Tyr Leu Gly Lys Pro Lys Ser Ser Asn
Leu Gln                         Tyr Leu Gly Lys Pro Lys Ser Ser Asn
```

Fig. 4

ISOLATED DNA ENCODING A PLANT RIBOSOME INACTIVATING PROTEIN FROM THE LEAVES OF SAPONARIA OFFICINALIS

This application is a Continuation of application Ser. No. 07/885,242, filed on May 20, 1992 now abandoned which was a continuation of application Ser. No. 07/302,901, filed on Jan. 30, 1989 now abandoned.

This invention relates to plant ribosome inactivating proteins and, more especially, to ribosome inactivating proteins of *Saponaria officinalis*.

Extracts from various plants inhibit protein synthesis of animal cells. In most cases, these are ribosome inactivating proteins (RIPs). RIPs can be classified in two distinct classes. Type 2 RIPs are toxins consisting of an active A-chain linked to a cell-binding B-chain, like ricin, abrin, moddecin and viscumin. Type 1 RIPs were extracted from *Phytolacca dodecandra, Phytolacca americana, Dianthus caryophyllus, Gelonium multiflorum, Momordica charantia, Saponaria officinalis*, and other plants. These are single-chain proteins with the biological activity of protein synthesis inhibition but without the cell-binding activity of type 2 RIPs. Without the ability to bind cells, they are non-toxic. In 1983, Stirpe et al reported on a type 1 RIP, SO-6, with excellent stability: it is lyophilisable and can remain dry at room temperature for long periods. In addition, overnight treatment at 37° C. with trypsin or chymotrypsin does not reduce RIP activity. This is an important property for a protein which must circulate through the bloodstream.

SO-6 is a protein of molecular weight 30 000. It has 40% amino acid sequence homology with the RIPs from *Phytolacca americana* in their N-terminal sequence, but is immunologically distinct from it and several other RIPs (Lappi et al, 1985). It is the major protein species of a family of proteins in the seed of *Saponaria officinalis* that are structurally highly related. They all cross react with the antisera raised against SO-6 (Lappi et al, 1986). Thorpe et al (1985) used SO-6 to make an immunotoxin that was tested in vivo against mouse AKR-A lymphoma solid tumours, with specific cytotoxicity to Thy-1.1- expressing cells both in tissue culture and animals.

Siena et al (1987) synthesised five immunotoxins by conjugating SO-6 to monoclonal antibodies that detected CD2, CD3 and CD5 T cell antigens, respectively. These immunotoxins bound to peripheral blood lymphocytes (PBL) and inhibited protein synthesis in a cell-free assay. After 2 hours at 37° C., mitogen-induced protein synthesis and cell proliferation was inhibited in a dose related manner, while unconjugated SO-6 or antibodies alone were not cytotoxic. Cytotoxicity was blocked by preincubation with unconjugated anti-CD5 but not with an irrelevant antibody, thus demonstrating that it was caused by specific binding to CD5+cells.

Recombinant DNA methodologies have been employed to construct fused genes between a toxin and a ligand. The first example of such construction was provided by Murphy et al (1986) who fused the genes coding for a truncated diphtheria toxin fragment and for melanocyte-stimulating hormone (alpha-MSH). The toxin-hormone chimeric gene direct the expression of a fused protein that retained the ADP-ribosyltransferase activity and lipid-associating domains of diphtheria toxin. However, the diphtheria toxin receptor-binding domain was replaced with MSH sequences. The chimeric toxin was found to be toxic for MSH receptor-positive human malignant melanoma cells in culture, while not being toxic for either Chinese hamster ovary or African green monkey kidney cells, both of which lack the alpha-MSH receptor.

More recently, Williams et al (1987) have extended these earlier observations by showing that fusion of the gene encoding interleukin-2 (IL-2) to a truncated diphtheria toxin gene also results in the expression of a biologically active chimeric IL-2 toxin. The fused protein was shown to be selectively targeted to activated or to malignant T cells carrying specific surface receptors for the ligand components of the hybrid, and was internalised by receptor-mediated endocytoses following in vitro binding to the IL-2 receptor.

A cloned Pseudomonas toxin (PE), from which the cell-recognition domain was deleted by site-directed mutagenesis, was fused to Transforming Growth Factor-alpha (TGF-alpha). The chimetic protein, purified from *E coli*, killed cells expressing epidermal growth factor receptors and had little activity against cells with few receptors (Chaudhary et al, 1987).

We have now cloned and expressed a gene encoding the type 1 RIP SO-6 of *Saponaria officinalis*. Accordingly, the present invention provides a DNA sequence:

```
      1                        24                              50
GTCACATCAA TCACATTAGATCTAGTAAATCCGACCGCGGGTCAATACTCATCTTTTGTG
                                 100
GATAAAATCCGAAACAACGTAAAGGATCCAAACCTGAAATACGGTGGTACCGACATAGCC
                                 150
GTGATAGGCCCACCTTCTAAAGAAAAATTCCTTAGAATTAATTTCCAAAGTTCCCGAGGA
                      200
ACGGTCTCACTTGGCCTAAAACGCGATAACTTGTATGTGGTCGCGTATCTTGCAATGGAT
      250                                                    300
AACACGAATGTTAATCGGGCATATTACTTCAGATCAGAAATTACTTCCGCCGAGTCAACC
                                 350
GCCCTTTTCCCAGAGGCCACAACTGCAAATCAGAAAGCTTTAGAATACACAGAAGATTAC
```

```
                                         400
AGTCGATTGAAAAGAATGCCCAGATAACACAAGGAGATCAAAGTAGAAAAGAACTCGGGT
                       450
TGGGGATTGACTTACTTTCAACGTCCATGGAAGCAGTGAACAAGAAGGCACGTGTGGTTA
                   500
AAGACGAAGCTAGATTCCTTCTTATCGCTATTCAGATGACGGCTGAGGCAGCGCGATTT
         550                                               600
AGGTACATACAAAACTTGGTAATCAAGAACTTTCCCAACAAGTTCAACTCGGAAAACAAA
                                     650
GTGATTCAGTTTGAGGTTAACTGGAAAAAAATTTCTACGGCAATATACGGGGATGCCAAA
                          700
AACGGCGTGTTTAATAAAGATTATGATTTCGGGTTTGGAA AAGTTAGGCAGGTGAAGGAC
                   750                    768
TTGCAAATGGGACTCCTTATGTATTTGGGCAAACCAAAGTCGTCAAAC.
```

This sequence may be preceded by a signal sequence. Preferably the signal sequence is:
ATGAAGATATATGTTGTAGCCACAATAG-
CATGGATCCTGCTTCAATTTTCAGCTTGG ACAA-
CAACTGATGCG.

A sequence may end with a termination codon such as TAG after the final codon AAC. Alternatively, this codon may be absent if it is wished to obtain a fusion protein comprising the RIP fused to a ligand/haptomer capable of binding to cells.

The DNA sequence coding for RIP SO-6 can be obtained by a method which comprises:

(i) isolating mRNA from *Saponaria officinalis*;
(ii) synthesising therefrom cDNA;
(iii) inserting the resulting cDNA into a cloning vector to obtain a cDNA library;
(iv) probing the cDNA library with a labelled DNA probe corresponding to a portion of the amino acid sequence of the said RIP to locate a clone comprising a said DNA sequence and
(v) optionally, isolating a DNA sequence comprising the said DNA sequence from the clone.

The mRNA is preferably extracted from the leaves or seeds of *Saponaria officinalis*. The cDNA can be prepared according to standard procedures. For example, synthesis of the first strand of the cDNA can be accomplished using reverse transcriptase. The second strand is typically synthesised using DNA polymerase followed by T4 polynucleotide kinase.

The cDNA is inserted into a cloning vector to obtain a cDNA library. The cloning vector may be a plasmid or phage viral vector. If the cloning vector is a plasmid, it may be a naturally-occurring plasmid or preferably a composite plasmid derived from fragments of other plasmids. The plasmid may contain a promoter sequence to improve the expression of the RIP gene. The cDNA library can be amplified in a suitable host, e.g. *E. coli*.

The library is probed by one or more labelled DNA sequence corresponding to a portion of the amino acid sequence of the RIP whose gene is being sought. The DNA probe sequences can be deduced from the amino acid sequence of the RIP if the DNA sequence of the RIP is not known. The probe sequences may correspond to the C-terminal or N-terminal portion of the RIP. The sequences may be up., to 120 bp long. A radioactive label can be employed.

In this way, one or more clones in the cDNA library may be located which comprise a DNA sequence coding for the desired RIP. This DNA sequence, or a longer DNA sequence comprising it, may be isolated using appropriate restriction endonucleases. The DNA sequence can then be cloned and expressed as desired.

In order to obtain RIP SO-6, a DNA sequence according to the invention is incorporated in an expression vector which is capable of expressing the RIP in a transformed host. The DNA sequence is provided in the expression vector operably linked to expression control elements, in particular a promoter. The vector typically has an origin of replication and a phenotypic marker. The DNA sequence to be expressed is provided between translational start and stop signals. The vector is typically a plasmid.

The DNA sequence may also comprise a further sequence encoding a ligand/haptomer capable of binding to cells, for example when it is wished to express an immunotoxin. The ligand/haptomer may be a monoclonal antibody which is specific for a tumor cell antigen or a F(ab')$_2$ fragment thereof. It may be an anti-T cell antibody. Other ligands/haptomers may be hormonal proteins which bind to specific receptor sites. The ligand/haptomer may alternatively be chemically conjugated to a RIP produced according to the invention to obtain an immunotoxin.

A host transformed with an expression vector according to the invention can be cultured to obtain the desired RIP or, when the DNA sequence incorporated in the expression vector further comprises a sequence encoding a ligand portion of an immunotoxin, the desired immunotoxin. An appropriate host may be employed, for example a plant or animal cell or a microoganism. A bacterial host such as *E. coli* may be employed. The RIP or immunotoxin thus expressed can be isolated from the culture by standard methods.

An immunotoxin, expressed as such or obtained by conjugating a ligand capable of binding to cells to expressed RIP, is generally formulated for administration with a pharmaceutically acceptable carrier or diluent. The immunotoxin may be administered by injection. In this event, it may be formulated with a sterile, pyrogen-free liquid such as Water for Injections or physiological saline.

The following Example illustrates the present invention. In the accompaning drawings.

EXAMPLE

1. Amino acid sequence of CNBr fragments of the Saponaria officinalis SO-6 RIP

SO-6 purification

SO-6 was prepared as previously described by Stirpe et al (1983).

CNBr cleavage and fragment purification

Ten milligrams of purified SO-6 were dissolved in 300 ul of 70% formic acid. About 30 mg of CNBr were added, and after 14–18 hours at room temperature the reaction mixture was diluted to 3 ml with deionised water and lyophilised. The resulting peptides were purified by gel filtration on Sephadex G-100 and hydrophobic reverse phase HPLC.

Amino acid and sequence analysis

Figure 1:
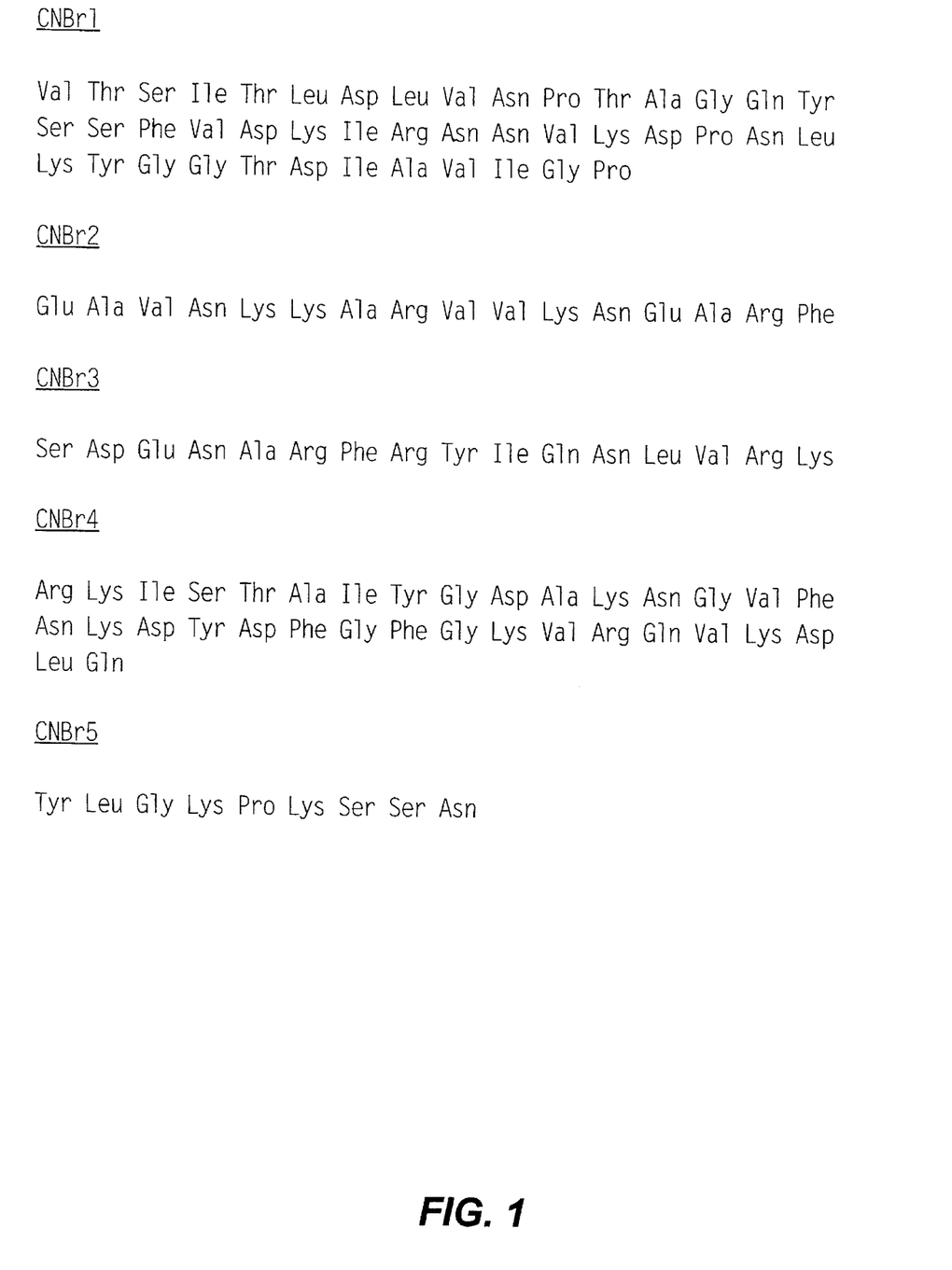
FIG. 1 shows the amino acid sequence of five CNBr fragments of SO-6.

Amino-acid analysis was carried out with the PICO-TAG analyser (Waters). Hydrolysis was performed in vacuo for 24 hours at 105° C. in constant boiling HCl containing 1% phenol. Sequence analysis was performed by a gas phase sequenator (Applied Biosystems). FIG. 1 shows the amino acid sequence of five CNBr fragments of SO-6. CNBr5 in the C-terminal CNBr fragment was identified by the lack of homoserine in the amino acid analysis.

2. cDNA Library Construction

RNA extraction

10–20 g of frozen leaves were homogenised with an Ultra Turrax for 5 minutes at top speed in 60 ml of 4.2 M guanidine-thiocyanate, 25 mM Na citrate, 5% Sarcosyl, 0.7 mM Mercaptoethanol, 0.01% antifoam, pH7. The homogenised slurry was filtered through a sterile cheese cloth and centrifuged at 5 000 rpm for 10 minutes at 4° C. The supernatant was layered over 5.7M CsCl, 25 mM Na acetate pH 5.4, 0.1M EDTA, and centrifuged at 31 000 rpm in a SW 40 rotor for 20 hours at 20° C. The total RNA pellet was washed with cold 70% ethanol and resuspended in a few millilitres of 10 mM Tris-HCl, 5 mM EDTA pH 7, extracted once with chloroform, salt adjusted to 0.3 M Na-acetate and precipitated with 2.5 volumes of cold ethanol. After 1 to several hours at -80° C. the RNA was centrifuged at 10 000 rpm for 1 hour in a Sorvall centrifuge. The pellet was washed with cold 70% ethanol and resuspended in binding buffer.

Approximately 1 mg of total RNA was recovered from each gram of leaves.

Poly(A)+ RNA was isolated by affinity chromatography on oligo (dT)-cellulose (Aviv and Leder, 1972).

Approximately 20 ug of Poly(A)+ RNA were recovered from 1 mg of total RNA. The length of the Poly(A)+ RNA was verified on a 1% agarose gel containing formaldehyde. The size of the RNA ranged from several Kb to a few hundred bases.

First strand cDNA synthesis

The first strand cDNA synthesis was carried out for 40 minutes at 42° C. in 50 ul of: 50 mM Tris-HCl buffer pH 8.5, 40 mM KCl, 10 mM $MgCl_2$, 0.4 mM DTT; 1 mM dATP; 1 mM dGTP; 1 mM dTTP; 0.5 mM dCTP; 0.1 mg/ml oligo (dT) $_{12-18}$; 25 U Human placental ribonuclease inhibitor; 20 uCi [alpha-$^{32}$P] dCTP 3000 Ci/mmol, 5 ug poly (A)+ RNA and 40 units of AMV reverse transcriptase.

Second strand cDNA synthesis

To the first strand cDNA reaction mixture, 93.5 ul of second strand buffer (100 mM HEPES pH 6.9, 100 mM KCl, 10 mM $MgCl_2$); 20 uCi [alpha-$^{32}$P] dCTP 3000 Ci/mmol; 4 U E coli ribonuclease H; 115 U E coli DNA polymerase I were added in a final volume of 250 ul.

The reaction mixture was incubated for 1 hour at 12° C., 1 hour at 22° C. and 10 minutes at 70° C. After the mixture was cooled down on ice, 10 U of T4 DNA polymerase were added,, and the mixture incubated at 37° C. for 10 minutes.

Addition of EcoRI linkers and EcoRI digestion

The cDNA was pur if led by phenol: chloroform (1:1) extraction and ethanol precipitation. 1 mg of phosphorylated EcoRI linkers were added to the double stranded cDNA preparation in a 20 ul reaction containing 66 mM Tris-HCl pH 7.5; 5 mM $MgCl_2$, 5 mM dithiothreitol, 1 mM ATP (ligation buffer) in the presence of 1 U of T4 DNA ligase. The mixture was incubated overnight at 12° C.

After addition of NaCl to 100 mM final concentration, spermidine to 2.5 mM and 30 units of ECO RI in a final volume of 100 ul, the mixture was incubated for 2 hours at 37° C.

The cDNA was purified from the non-incorporated linkers passing it through a Sepharose 4B column in 0.3 M NaCl, 10 mM Tris-HCl pH8, 1 mM EDTA. cDNA fractions ranging in size between 8 Kb and 0.5 Kb were pooled and ethanol precipitated.

Ligation of cDNA to λgt 10 arms and in vitro packaging 0.5 ug of λgt 10 arms were ligated to cDNA with 2.5 units of T4 DNA ligase in ligation buffer with a final volume of 5 ul and incubated overnight at 15° C.

The DNA was then ethanol precipitated and carefully resuspended in 2.5 ul of 10 mM Tris-HCl pH 7.5, 1 mM EDTA for in vitro packaging with an in vitro packaging mixture ( Amersham ).

The library obtained was amplified using E coli NM514 host. The number of independent clones obtained was 3.3× $10^{10}$ with a background of non-recombinant phases of 36%.

3. cDNA library screening

Synthesis of oligonucleotides a—Synthesis of a 111 bp long oligonucleotide.

This long oligonucleotide corresponded to the first 37 amino acids at the $NH_2$ terminal of SO-6 RIP. The codon usage was chosen based on the codon frequency of the seed storage proteins sequenced so far as deduced from sequence databases (GenBank). The long oligonucleotide was synthesised using an Applied Biosystems Inc Mod 380B automatic DNA synthesiser, purified by reverse-phase HPLC and assembled in double stranded form using 8 different oligonucleotides (19 to 28 bases long).

The oligonucleotides were ligated together and the resulting double stranded oligonucleotide was inserted into the SmaI site of M13mp8 and sequenced in order to verify the nucleotide sequence.

b—Synthesis of short oligonucleotides.

A mixture of 16 short (21 bases) oligonucleotides, corresponding to CNBr fragment of the C-termini of SO-6, was synthesised using the same Applied Biosystem Inc synthesiser described above.

Labelling of oligonucleotides a—111 bp "long" oligonucleotide.

This oligonucleotide, inserted into the ss DNA phage M13mp8 as described, was labelled by DNA polymerase after annealing to a primer complementary to the M13 sequence adjacent to the oligonucleotide. About 6 ug of primer were annealed to 5 ug of M13mp8-111 oligonucleotide in 7 mM Tris-HCl pH 7.5, 7 mM $MgCl_2$, 50 mM NaCl, 10 mM DTT, 0.1 mM EDTA pH 8.0 (1× klenow buffer) in a volume of 30 ul for 1 hour at 60° C. 50 ul of [alpha - $^{32}$p] dCTP 3.000 Ci/mmol, dCTP, dTTP, dATP at a final 50 uM concentration and 5 units of DNA poymerase (klenow fragment) were added in a final volume of 45 ul.

After incubation at room temperature for 15 minutes, 1 ul of 1 mM dCTP was added and the mixture incubated again for 15 minutes at RT.

The enzyme was inactivated at 70° C. for 10 minutes. After addition of 1.3 ul of 5M NaCl and 20 units of each Eco RI and Bam HI, the mixture was incubated for 2 hours at 37° C. in order to cut the 111 bp long oligonucleotide out of the phage vector. The oligonucleotide was then separated from the vector on a 3.5% PAGE and eluted overnight in H$_2$O at 37° C. The specific activity was about 5×10$^8$ DPM/ug DNA.

b—"Short" mixed oligonucleotides.

The mixture of short (21 bp) oligonucleotides was end-labelled using T4 polynucleotide kinase as described by Davies et al, 1986.

Plaque hybridisation using the oligonucleotides as probes
a—Screening of the cDNA library with the 111 bp long oligonucleotide.

About 200 000 phages were plated on a lawn of *E coli* NM514 cells. After an overnight growth at 37° C. the recombinant phages were transferred in duplicate nitrocellulose filters, their DNA was denatured, neutralised and baked under vacuum at 80° C. for 2 hours.

The filters were prehybridised in 6× SSC, 5× Denhardt's, 0.1% SDS, 100 ug/ml salmon sperm DNA at 50° C. for 2 hours.

The filters were then hybridised overnight at 50° C. in the same mixture with the addition of 1×10$^6$ cpm/ml of labelled probe (probe a). The filters were washed in 0.1 × SSC, 0.1% SDS at 60° C. and autoradiographed.

Positive phage phaques were isolated and screened again twice in order to isolate single clones.

b—Screening of the positive clones with the oligonucleotide mixture (probe b).

The clones that hybridised to the 111 bp probe were plated and screened with the labelled "short" oligonucleotide mixture.

The filters were prehybridised in 6× SSC, 5× Denhardt's, 0.1% SDS, 100 ug/ml salmon sperm DNA at 42° C.

The filters were then hybridised overnight at 42° C after addition of the labelled oligonucleotide mixture.

The filters were then washed in 6× SSC, 0.1% SDS at 45° C. and autoradiographed. One of the clones positive to both probes was isolated and sequenced.

DNA sequencing

Figure 2:
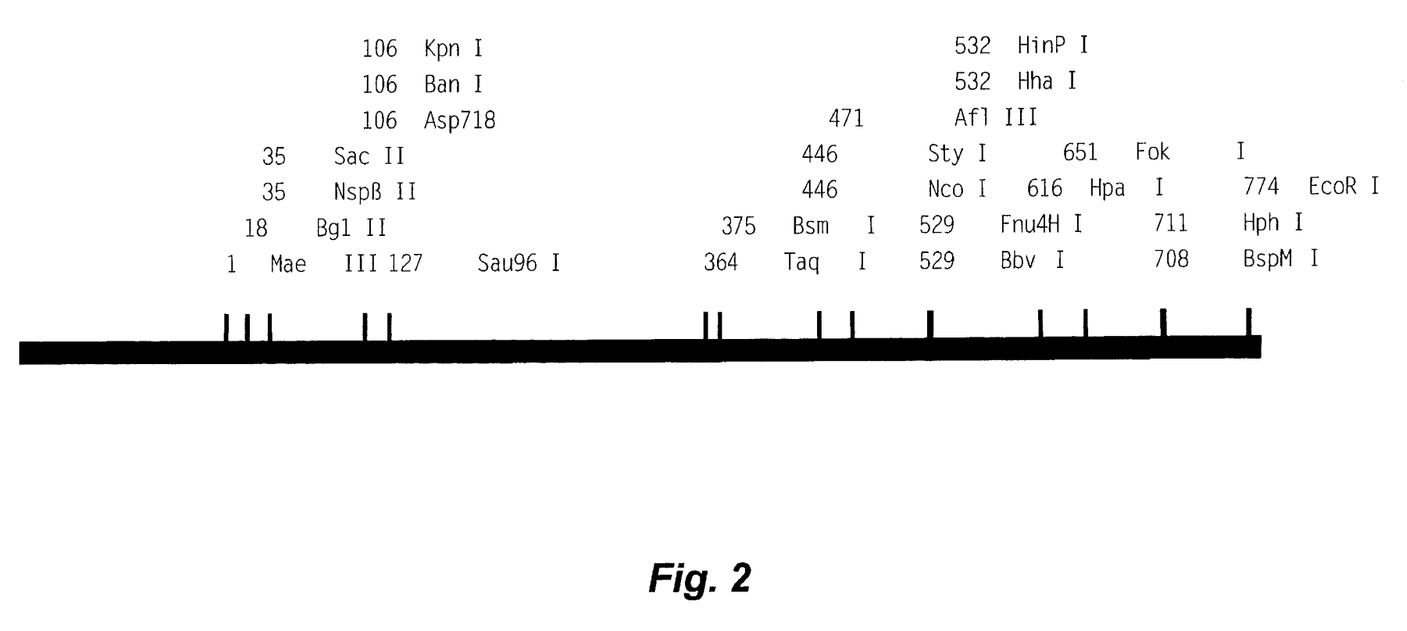
FIG. 2 is a restriction map of the EcoRI insert of clone pBL6.

The DNA of the positive clone pBL6 was isolated by the Promega LambdaSorb phage adsorbent method, the insert was removed with EcoRI and ligated to the EcoRI site of M13mp8 in both directions. The restriction endonuclease map of pBL6 clone is shown in FIG. 2. Sequencing was carried out by the Sanger procedure. Both strands of the gene were sequenced, revealing an open reading frame coding for a protein of 280 amino acids.

Figure 3B:
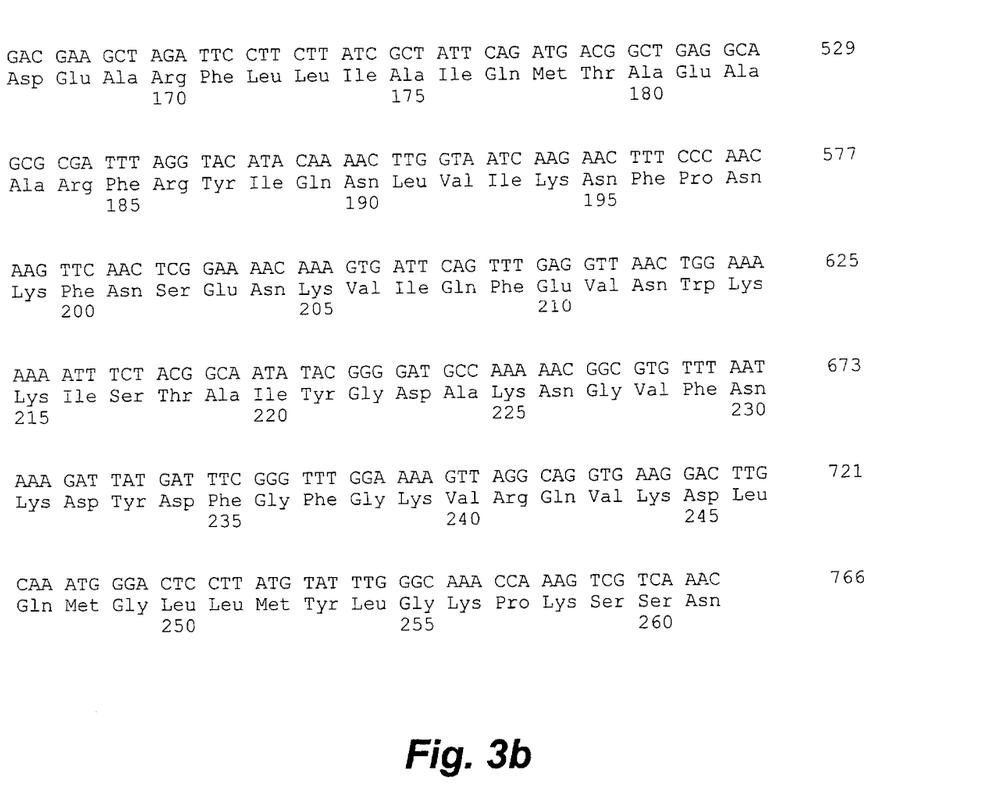
FIG. 3 shows the DNA sequence and the predicted corresponding amino acid sequence of the EcoRI insert of clone pBL6, and FIG. 4 compares the CNBr fragments of SO-6 with the predicted amino acid sequence.

Comparing the published N-terminal amino acid sequence of SO-6 as reported by Lappi et al (1985) to that of clone pBL6, we could predict the amino acid sequence start point of the mature protein encoded by our clone (FIG. 3). The translation initiation site was assigned to the methionine codon d(ATG) present at nucleotide residues −72 to −70. The sequence also predicts an N-terminal extension of 24 amino acids for the signal peptide. This data is in agreement with the length (24 amino acids) of the ricin signal peptide. However, comparison of the CNBr fragments of SO-6 to the predicted amino acid sequence of clone pBL6 showed six differences at single amino acid residues (FIG. 4). This could be due to mistakes in amino acid sequencing, or to sequence heterogeneities in the RIPs purified from *Saponaria officinalis* (Stirpe et al, 1983).

4. Expression in *E. coli*

Starting from the SO-6 gene carried by clone pBL6, the 900 bp EcoRI fragment (FIG. 2) was subcloned into the EcoRI site of the vector pUC 8 (Amersham, U.K.). The plasmid thus obtained was then cut out with Bgl II and Pst I, allowing retrieval of a fragment containing the SO-6 gene but lacking the 5' region encoding the signal peptide and the first 6 amino acid residues (FIG. 2 and 3). At the 3' end of the fragment the SO-6 cDNA was followed by an extra piece of DNA deriving from the pUC 8 polylinker between the EcoRI and the Pst I site.

Ligation of the Bgl II-Pst I fragment carrying the gene for SO-6 to the expression vector pUEX3 (Bressan and Stanley, 1987) cut with BamHI and Pst I, resulted in an in-frame fusion between the gene coding for beta-galactosidase (Stanley and Luzio, 1984) and the gene containing most of the coding sequence for SO-6. Downstream from the SO-6 gene, translation termination was provided by stop codons present in the pUEX3 vector.

The recombinant plasmid thus obtained was transformed into the bacterial host *E. coli* DM105 (Amersham, UK). The hybrid gene, under the control of the lambda $R_R$ promoter, was expressed essentially in accordance with Zabeau and Stanley (1982). Bacteria were grown at 30° C. to OD$_{600}$ 0.9.The temperature was quickly raised to 42° C. by addition of an equal volume of broth pre-heated at 54° C. Cultures were incubated at 42° C. for 2 hours before harvest. Total cell lysates were loaded on polyacylamide slab gels (at the appropriate concentration) using the Laemmli method. For the immunoblotting, the gels were transferred on nitrocellulose filters using a transblot apparatus (Bio-Rad) at 0.2 A for 4 hours at 4° C. in 25 mM Tris Base, 192 mM Glycine, 20% Methanol. After transfer the filters were washed with distilled water and then incubated 1 hour with PBS +3% BSA with gentle shaking. Filters were washed again with distilled water and incubated with an anti-SO-6 antiserum raised in rabbits diluted 1:250 with PBS, and incubated 1 hour at room temperature. After 2 washes with PBS and PBS +0.05% Tween 20, the filters were incubated with an anti rabbit IgG raised in goat conjugated with horseradish peroxidase (Bio-Rad) diluted 1:7500 for 1 hour at room temperature. After two more washes, filters were stained with 4-chloro-1-napthol.

Using these procedures, the molecular weight of the hybrid beta galactosidase —SO-6 protein was found to be, as expected, 145 Kd on SDS-PAGE. The band migrating at this position on the gel was specifically recognized by an anti-SO-6 antiserum by the immunoblot procedure described above.

The following method was used for the purification of the hybrid protein. Bacterial pellets from 100 ml culture were resuspended in 3–5 ml of buffer A (50 mM Tris/HCl pH 7.4, 170 mM NaCl, 2.5 mg/ml lysozyme), incubated 30 min in ice and sonicated 5 times for 20 Sec on ice. After centrifugation (10,000 rpm, 40 rain at 4° C. in a Sorvall SS34 rotor), the pellet was resuspended in 10 ml of buffer B (7M urea, 10 mM Tris-HCl pH 7.4, 1 mM EDTA) and left at room temperature for 30 min. The suspension was centrifuged as above and the supernatant was dialysed extensively at 4° C. against 2 l of 50 mM Tris HCl pH 7.4.

Purification was achieved by affinity chromatography on p-aminophenyl thiogalactoside-Sepharose as described by Ullman (1984). SDS-PAGE of the purified material was run in parallel to the unpurified material as described above, and revealed a prominent band of the expected molecular weight that was recognized by the specific anti-SO-6 antiserum after immunoblotting by the procedure already described. The purified recombinant protein corresponded in migration to the hybrid beta galactosidase-SO6 present in extracts of the induced *E. coli* strain.

REFERENCES

Aviv and Leder, Proc. Natl. Acad. Sci. USA, 69 (1972) 1408.
Bressan and Stanley, Nucleic Acid Research 15, 10056, 1987.
Chaudhary et al, Proc. Natl. Acad. Sci. USA, 84 (1987) 4538–4542.
Davis et al, Basic methods in molecular biology, 1986, Elsevier Science Publishing Co., Inc.
Lappi et al, Biochem. Biophys. Res. Comm., 129 (1985) 934–942.
Lappi et al, Abs. 15th annual UCLA Symposia on Molecular and Cellular Biology, Park Utah, Feb. 22, Mar. 23, 1986.
Murphy et al, Proc. Natl. Acad. Sci., USA, 83 (1986) 8258–8262.
Siena et al, Abst. American Assoc. Cancer Res., Atlanta, Ga., 1987.
Stanley and Luzio, EMBO Journal 3, 1429–1434, 1984.
Stirpe et al, Biochem. J., 216 (1983) 617–625.
Thorpe et al, J. N. C. I., 75 (1985) 151–159.
Uillmann, Gene 29, 27–31, 1984.
Williams et al, Abst. Int. Syrup. "Protein Engineering'87", Oxford, UK, 5–8 Apr., 1987.
Zabeau and Stanley, EMBO Journal 1, 1217–1224, 1982.

We claim:

1. An isolated and purified DNA fragment, having nucleotides that encode ribosomal inactivating protein (RIP) SO-6 and that have the following sequence:

```
1                               24
GTCACATCAA TCACATTAGA TCTAGTAAAT
                  50
CCGACCGCGG GTCAATACTC ATCTTTTGTG
GATAAAATCC GAAACAACGT AAAGGATCCA
                 100
AACCTGAAAT ACGGTGGTAC CGACATAGCC
                               150
GTGATAGGCC CACCTTCTAA AGAAAAATTC
CTTAGAATTA ATTTCCAAAG TTCCCGAGGA
                 200
ACGGTCTCAC TTGGCCTAAA ACGCGATAAC
TTGTATGTGG TCGCGTATCT TGCAATGGAT
                 250
AACACGAATG TTAATCGGGC ATATTACTTC
                               300
AGATCAGAAA TTACTTCCGC CGAGTCAACC
GCCCTTTTCC CAGAGGCCAC AACTGCAAAT
                               350
CAGAAAGCTT TAGAATACAC AGAAGATTAT
CAGTCGATTG AAAAGAATGC CCAGATAACA
                 400
CAAGGAGATC AAAGTAGAAA AGAACTCGGG
                               450
TTGGGGATTG ACTTACTTTC AACGTCCATG
GAAGCAGTGA ACAAGAAGGC ACGTGTGGTT
                 500
AAAGACGAAG CTAGATTCCT TCTTATCGCT
ATTCAGATGA CGGCTGAGGC AGCGCGATTT
                 550
AGGTACATAC AAAACTTGGT AATCAAGAAC
                               600
TTTCCCAACA AGTTCAACTC GGAAAACAAA
GTGATTCAGT TTGAGGTTAA CTGGAAAAAA
                 650
ATTTCTACGG CAATATACGG GGATGCCAAA
AACGGCGTGT TTAATAAAGA TTATGATTTC
                 700
GGGTTTGGAA AAGTTAGGCA GGTGAAGGAC
                               750
TTGCAAATGG GACTCCTTAT GTATTTGGGC
                 768
AAACCAAAGT CGTCAAAC.
```

2. An isolated and purified DNA fragment, encoding a signal sequence and the sequence of nucleotides of the DNA fragment of claim 1 that encodes SO-6, wherein:

the nucleotides encoding the signal sequence are directly linked to the 5' end of the nucleotides that encode the RIP SO-6 of claim 1; and the nucleotides encoding the signal sequence have the following sequence:
ATGAAGATATATGTTGTAGCCACAATAG-CATGGATCCTGCTTCAATTTTCAGCTTGG ACAA-CAACTGATGCG.

3. An isolated and purified DNA fragment encoding a precursor of ribosomal inactivating protein (RIP) SO-6 that has the following amino acid sequence:

| | | | | | | | | | | |
|---|---|---|---|---|---|---|---|---|---|---|
| Met | Lys | Ile | Tyr | Val | Val | Ala | Thr | Ile | Ala | Trp |
| | | | | −20 | | | | | −15 | |
| Ile | Leu | Leu | Gln | Phe | Ser | Ala | Trp | Thr | Thr | Thr |
| | | | −10 | | | | | −5 | | |
| Asp | Ala | Val | Thr | Ser | Ile | Thr | Leu | Asp | Leu | Val |
| | | 1 | | | | 5 | | | | |
| Asn | Pro | Thr | Ala | Gly | Gln | Tyr | Ser | Ser | Phe | Val |
| 10 | | | | | 15 | | | | | 20 |

-continued

| | | | | | | | | | |
|---|---|---|---|---|---|---|---|---|---|
| Asp | Lys | Ile | Arg | Asn 25 | Asn | Val | Lys | Asp 30 | Asn |
| Leu | Lys | Tyr | Gly 35 | Gly | Thr | Asp | Ile | Ala 40 | Val Ile |
| Gly | Pro | Pro 45 | Ser | Lys | Glu | Lys | Phe 50 | Leu | Arg Ile |
| Asn | Phe 55 | Gln | Ser | Ser | Arg | Gly 60 | Thr | Val | Ser Leu |
| Gly 65 | Leu | Lys | Arg | Asp | Asn 70 | Leu | Tyr | Val | Val Ala 75 |
| Tyr | Leu | Ala | Met | Asp 80 | Asn | Thr | Asn | Val | Asn Arg 85 |
| Ala | Tyr | Tyr | Phe 90 | Arg | Ser | Glu | Ile | Thr 95 | Ser Ala |
| Glu | Ser | Thr 100 | Ala | Leu | Phe | Pro | Glu 105 | Ala | Thr Thr |
| Ala | Asn 110 | Gln | Lys | Ala | Leu | Glu 115 | Tyr | Thr | Glu Asp |
| Tyr 120 | Gln | Ser | Ile | Glu | Lys 125 | Asn | Ala | Gln | Ile Thr 130 |
| Gln | Gly | Asp | Gln | Ser 135 | Arg | Lys | Glu | Leu | Gly 140 Leu |
| Gly | Ile | Asp | Leu 145 | Leu | Ser | Thr | Ser | Met 150 | Glu Ala |
| Val | Asn | Lys 155 | Lys | Ala | Arg | Val | Val 160 | Lys | Asp Glu |
| Ala | Arg 165 | Phe | Leu | Leu | Ile | Ala 170 | Ile | Gln | Met Thr |
| Ala 175 | Glu | Ala | Ala | Arg | Phe 180 | Arg | Tyr | Ile | Gln Asn 185 |
| Leu | Val | Ile | Lys | Asn 190 | Phe | Pro | Asn | Lys | Phe 195 Asn |
| Ser | Glu | Asn | Lys 200 | Val | Ile | Gln | Phe | Glu 205 | Val Asn |
| Trp | Lys | Lys 210 | Ile | Ser | Thr | Ala | Ile 215 | Tyr | Gly Asp |
| Ala | Lys 220 | Asn | Gly | Val | Phe | Asn 225 | Lys | Asp | Tyr Asp |
| Phe 320 | Gly | Phe | Gly | Lys | Val 235 | Arg | Gln | Val | Lys Asp 240 |
| Leu | Gln | Met | Gly | Leu 245 | Leu | Met | Tyr | Leu | Gly 250 Lys |
| Pro | Lys | Ser | Ser | Asn. 255 | | | | | |

4. An isolated and purified DNA fragment encoding ribosomal inactivating protein (RIP) SO-6 that has the following amino acid sequence:

| | | | | | | | | | |
|---|---|---|---|---|---|---|---|---|---|
| Val 1 | Thr | Ser | Ile | Thr 5 | Leu | Asp | Leu | Val | Asn Pro 10 |
| Thr | Ala | Gly | Gln 15 | Tyr | Ser | Ser | Phe | Val 20 | Asp Lys |
| Ile | Arg | Asn 25 | Asn | Val | Lys | Asp | Pro 30 | Asn | Leu Lys |
| Tyr | Gly 35 | Gly | Thr | Asp | Ile | Ala 40 | Val | Ile | Gly Pro |
| Pro 45 | Ser | Lys | Glu | Lys | Phe 50 | Leu | Arg | Ile | Asn Phe 55 |
| Gln | Ser | Ser | Arg | Gly 60 | Thr | Val | Ser | Leu | Gly 65 Leu |
| Lys | Arg | Asp | Asn 70 | Leu | Tyr | Val | Val | Ala 75 | Tyr Leu |
| Ala | Met | Asp 80 | Asn | Thr | Asn | Val | Asn 85 | Arg | Ala Tyr |
| Tyr | Phe 90 | Arg | Ser | Glu | Ile | Thr 95 | Ser | Ala | Glu Ser |
| Thr 100 | Ala | Leu | Phe | Pro | Glu 105 | Ala | Thr | Thr | Ala Asn 110 |
| Gln | Lys | Ala | Leu | Glu 115 | Tyr | Thr | Glu | Asp | Tyr 120 Gln |
| Ser | Ile | Glu | Lys 125 | Asn | Ala | Gln | Ile | Thr 130 | Gln Gly |
| Asp | Gln | Ser 135 | Arg | Lys | Glu | Leu | Gly 140 | Leu | Gly Ile |
| Asp | Leu 145 | Leu | Ser | Thr | Ser | Met 150 | Glu | Ala | Val Asn |
| Lys 155 | Lys | Ala | Arg | Val | Val 160 | Lys | Asp | Glu | Ala Arg 165 |
| Phe | Leu | Leu | Ile | Ala 170 | Ile | Gln | Met | Thr | Ala 175 Glu |
| Ala | Ala | Arg | Phe 180 | Arg | Tyr | Ile | Gln | Asn 185 | Leu Val |
| Ile | Lys | Asn 190 | Phe | Pro | Asn | Lys | Phe 195 | Asn | Ser Glu |
| Asn | Lys 200 | Val | Ile | Gln | Phe | Glu 205 | Val | Asn | Trp Lys |
| Lys | Ile 210 | Ser | Thr | Ala | Ile | Tyr 215 | Gly | Asp | Ala Lys 220 |
| Asn | Gly | Val | Phe | Asn 225 | Lys | Asp | Tyr | Asp | Phe 320 Gly |
| Phe | Gly | Lys | Val 235 | Arg | Gln | Val | Lys | Asp 240 | Leu Gln |
| Met | Gly | Leu 245 | Leu | Met | Tyr | Leu | Gly 250 | Lys | Pro Lys |
| Ser | Ser | Asn. 255 | | | | | | | |

5. A vector, containing the DNA fragment of claim 3.

* * * * *

UNITED STATES PATENT AND TRADEMARK OFFICE
CERTIFICATE OF CORRECTION

PATENT NO.    : 5,529,932
DATED         : June 25, 1996
INVENTOR(S)   : Rolando Lorenzetti et al.

It is certified that error appears in the above identified patent and that said Letters Patent is hereby corrected as shown below:

On the title page at [54] Inventors, line 3: delete "Dian" and insert therefor --Dani--.

Signed and Sealed this

Twenty-second Day of October, 1996

Attest:

BRUCE LEHMAN

*Attesting Officer*        *Commissioner of Patents and Trademarks*